(12) United States Patent
Wolinsky et al.

(10) Patent No.: US 7,572,228 B2
(45) Date of Patent: Aug. 11, 2009

(54) DEVICES FOR FIXING A SENSOR IN A LUMEN

(75) Inventors: Lone Wolinsky, Ramat Gan (IL); Alon Ben-Yoseph, Amek Yisrael (IL); Abraham Penner, Tel Aviv (IL)

(73) Assignee: Remon Medical Technologies Ltd, Caesarea (IL)

( * ) Notice: Subject to any disclaimer, the term of this patent is extended or adjusted under 35 U.S.C. 154(b) by 0 days.

(21) Appl. No.: 11/034,502

(22) Filed: Jan. 12, 2005

(65) Prior Publication Data

US 2005/0154321 A1     Jul. 14, 2005

Related U.S. Application Data

(60) Provisional application No. 60/536,580, filed on Jan. 13, 2004.

(51) Int. Cl.
*A61B 5/00* (2006.01)

(52) U.S. Cl. .................. 600/486; 600/549; 600/481; 600/309; 600/345; 600/347; 600/365; 600/300

(58) Field of Classification Search .................. 600/486
See application file for complete search history.

(56) References Cited

U.S. PATENT DOCUMENTS

| 3,874,388 | A |   | 4/1975  | King et al.       |
|-----------|---|---|---------|-------------------|
| 4,485,813 | A |   | 12/1984 | Anderson et al.   |
| 4,836,204 | A |   | 6/1989  | Landymore et al.  |
| 4,846,191 | A |   | 7/1989  | Brockway et al.   |
| 4,900,303 | A |   | 2/1990  | Lemelson          |
| 4,917,089 | A |   | 4/1990  | Sideris           |
| 5,040,538 | A |   | 8/1991  | Mortazavi         |
| 5,218,965 | A | * | 6/1993  | Ring .......... 600/486 |
| 5,284,138 | A | * | 2/1994  | Kujawski ...... 600/486 |
| 5,334,217 | A |   | 8/1994  | Das               |
| 5,411,551 | A |   | 5/1995  | Winston et al.    |
| 5,415,630 | A |   | 5/1995  | Gory et al.       |
| 5,451,235 | A |   | 9/1995  | Lock et al.       |
| 5,604,531 | A |   | 2/1997  | Iddan et al.      |
| 5,634,936 | A |   | 6/1997  | Linden et al.     |
| 5,656,036 | A |   | 8/1997  | Palmaz            |
| 5,662,711 | A |   | 9/1997  | Douglas           |

(Continued)

FOREIGN PATENT DOCUMENTS

EP          0897690           2/1999

(Continued)

OTHER PUBLICATIONS

PCT International Search Report for PCT/US2005/000041, Applicant: Ramon Medical Technologies Ltd, Forms PCT/ISA/210 and 220, dated Apr. 21, 2005 (7 pages).

(Continued)

*Primary Examiner*—Robert L Nasser
(74) *Attorney, Agent, or Firm*—Faegre & Benson LLP

(57) ABSTRACT

Apparatus for positioning at least one sensor in a body lumen, the apparatus including a fixation element, a sensor, and a connecting element that connects the sensor to the fixation element, the connecting element extending at least partially into the lumen so that the sensor is located radially inward from a wall of the lumen.

29 Claims, 4 Drawing Sheets

U.S. PATENT DOCUMENTS

| | | | |
|---|---|---|---|
| 5,704,352 | A | 1/1998 | Tremblay et al. |
| 5,725,552 | A | 3/1998 | Kotula et al. |
| 5,733,313 | A | 3/1998 | Barreras, Sr. et al. |
| 5,772,669 | A | 6/1998 | Vrba |
| 5,775,331 | A | 7/1998 | Raymond et al. |
| 5,833,603 | A | 11/1998 | Kovacs et al. |
| 5,855,563 | A | 1/1999 | Kaplan et al. |
| 5,860,923 | A | 1/1999 | Lenker et al. |
| 5,967,986 | A | 10/1999 | Cimochowski et al. |
| 5,967,989 | A | 10/1999 | Cimochowski et al. |
| 6,002,969 | A | 12/1999 | Machek et al. |
| 6,015,386 | A | 1/2000 | Kensey et al. |
| 6,015,387 | A | 1/2000 | Schwartz et al. |
| 6,030,413 | A | 2/2000 | Lazarus |
| 6,033,366 | A | 3/2000 | Brockway et al. |
| 6,053,873 | A | 4/2000 | Govari et al. |
| 6,076,016 | A | 6/2000 | Feierbach |
| 6,097,984 | A | 8/2000 | Douglas |
| 6,140,740 | A | 10/2000 | Porat et al. |
| 6,159,156 | A | 12/2000 | Van Bockel |
| 6,179,858 | B1 | 1/2001 | Squire et al. |
| 6,193,745 | B1 | 2/2001 | Fogarty et al. |
| 6,240,312 | B1 | 5/2001 | Alfano et al. |
| 6,277,078 | B1 | 8/2001 | Porat et al. |
| 6,309,350 | B1 | 10/2001 | Van Tassel |
| 6,328,699 | B1 | 12/2001 | Eigler et al. |
| 6,331,163 | B1 * | 12/2001 | Kaplan .................... 600/486 |
| 6,379,308 | B1 | 4/2002 | Brockway et al. |
| 6,409,674 | B1 | 6/2002 | Brockway et al. |
| 6,416,474 | B1 | 7/2002 | Penner et al. |
| 6,432,050 | B1 | 8/2002 | Porat et al. |
| 6,442,413 | B1 * | 8/2002 | Silver .................... 600/345 |
| 6,447,522 | B2 | 9/2002 | Gambale et al. |
| 6,475,170 | B1 | 11/2002 | Doran et al. |
| 6,486,588 | B2 | 11/2002 | Doron et al. |
| 6,527,780 | B1 | 3/2003 | Wallace et al. |
| 6,585,763 | B1 | 7/2003 | Keilman et al. |
| 6,592,553 | B2 | 7/2003 | Zhang et al. |
| 6,628,989 | B1 | 9/2003 | Penner et al. |
| 6,645,143 | B2 | 11/2003 | VanTassel et al. |
| 6,699,186 | B1 | 3/2004 | Wolinsky et al. |
| 6,702,847 | B2 | 3/2004 | DiCarlo |
| 6,730,108 | B2 | 5/2004 | Van Tassel et al. |
| 6,738,671 | B2 | 5/2004 | Christophersom et al. |
| 6,743,173 | B2 | 6/2004 | Penner et al. |
| 6,746,404 | B2 | 6/2004 | Schwartz |
| 6,764,446 | B2 | 7/2004 | Wolinsky et al. |
| 6,783,499 | B2 | 8/2004 | Schwartz |
| 6,800,060 | B2 | 10/2004 | Marshall |
| 6,840,956 | B1 | 1/2005 | Wolinsky et al. |
| 6,855,115 | B2 | 2/2005 | Fonseca et al. |
| 6,890,303 | B2 | 5/2005 | Fitz |
| 6,904,308 | B2 | 6/2005 | Frisch et al. |
| 6,926,670 | B2 | 8/2005 | Rich |
| 6,934,573 | B1 | 8/2005 | Glukhovsky et al. |
| 6,950,690 | B1 | 9/2005 | Meron et al. |
| 6,958,034 | B2 | 10/2005 | Iddan |
| 6,972,017 | B2 | 12/2005 | Smith et al. |
| 6,984,205 | B2 | 1/2006 | Gazdzinski |
| 7,001,329 | B2 | 2/2006 | Kobayashi et al. |
| 7,006,858 | B2 | 2/2006 | Silver et al. |
| 7,009,634 | B2 | 3/2006 | Iddan et al. |
| 7,011,671 | B2 | 3/2006 | Welch |
| 7,024,248 | B2 | 4/2006 | Penner et al. |
| 7,033,322 | B2 * | 4/2006 | Silver .................... 600/486 |
| 7,035,684 | B2 | 4/2006 | Lee |
| 7,039,453 | B2 | 5/2006 | Mullick et al. |
| 7,060,038 | B2 | 6/2006 | Letort et al. |
| 7,065,409 | B2 | 6/2006 | Mazar |
| 7,083,822 | B2 | 8/2006 | Brightbill |
| 7,116,352 | B2 | 10/2006 | Yaron |
| 7,118,529 | B2 | 10/2006 | Glukhovsky et al. |
| 7,160,258 | B2 | 1/2007 | Imran et al. |
| 7,181,261 | B2 | 2/2007 | Silver et al. |
| 7,198,603 | B2 | 4/2007 | Penner et al. |
| 7,283,874 | B2 | 10/2007 | Penner |
| 7,308,319 | B2 | 12/2007 | Lovett et al. |
| 7,347,868 | B2 | 3/2008 | Burnett et al. |
| 7,437,193 | B2 | 10/2008 | Parramon et al. |
| 2002/0077555 | A1 * | 6/2002 | Schwartz .................... 600/486 |
| 2002/0183628 | A1 * | 12/2002 | Reich et al. .................. 600/486 |
| 2002/0188207 | A1 * | 12/2002 | Richter ........................ 600/486 |
| 2003/0114897 | A1 | 6/2003 | Von Arx et al. |
| 2004/0147969 | A1 | 7/2004 | Mann et al. |
| 2005/0080346 | A1 * | 4/2005 | Gianchandani et al. ..... 600/486 |
| 2005/0115561 | A1 | 6/2005 | Stahmann et al. |
| 2005/0124875 | A1 | 6/2005 | Kawano et al. |
| 2005/0136385 | A1 | 6/2005 | Mann et al. |
| 2005/0149108 | A1 | 7/2005 | Cox |
| 2005/0149128 | A1 | 7/2005 | Heil, Jr. et al. |
| 2005/0149155 | A1 | 7/2005 | Scheiner et al. |
| 2005/0149156 | A1 | 7/2005 | Libbus et al. |
| 2005/0165456 | A1 | 7/2005 | Mann et al. |
| 2005/0245840 | A1 | 11/2005 | Christopherson et al. |
| 2006/0047205 | A1 | 3/2006 | Ludomirsky et al. |
| 2006/0064133 | A1 | 3/2006 | Von Arx et al. |
| 2006/0064134 | A1 | 3/2006 | Mazar et al. |
| 2006/0064142 | A1 | 3/2006 | Chavan et al. |
| 2006/0064143 | A1 | 3/2006 | Von Arx et al. |
| 2006/0079740 | A1 | 4/2006 | Silver et al. |
| 2006/0089627 | A1 | 4/2006 | Burnett et al. |
| 2006/0089694 | A1 | 4/2006 | Zhang et al. |
| 2006/0122522 | A1 | 6/2006 | Chavan et al. |
| 2006/0149329 | A1 | 7/2006 | Penner |
| 2006/0149330 | A1 | 7/2006 | Mann et al. |
| 2006/0178586 | A1 | 8/2006 | Dobak, III |
| 2006/0206153 | A1 | 9/2006 | Libbus et al. |
| 2006/0287700 | A1 | 12/2006 | White et al. |
| 2006/0293741 | A1 | 12/2006 | Johnson et al. |
| 2007/0049833 | A1 | 3/2007 | Tearney et al. |
| 2007/0129637 | A1 | 6/2007 | Wolinsky et al. |
| 2007/0156205 | A1 | 7/2007 | Larson et al. |
| 2007/0162090 | A1 | 7/2007 | Penner |
| 2007/0179583 | A1 | 8/2007 | Goetzinger et al. |
| 2007/0274565 | A1 | 11/2007 | Penner |
| 2008/0071178 | A1 | 3/2008 | Greenland et al. |
| 2008/0071248 | A1 | 3/2008 | Delgado et al. |
| 2008/0071339 | A1 | 3/2008 | Stalker et al. |
| 2008/0108904 | A1 | 5/2008 | Heil |

FOREIGN PATENT DOCUMENTS

| | | |
|---|---|---|
| EP | 0 928 598 | 7/1999 |
| EP | 1068836 | 1/2001 |
| EP | 1488735 | 6/2007 |
| GB | 2333044 | 7/1999 |
| WO | WO83/03348 | 10/1983 |
| WO | WO 99/34731 | 7/1999 |
| WO | WO00/16686 | 3/2000 |
| WO | WO01/67989 | 9/2001 |
| WO | WO 01/87137 | 11/2001 |
| WO | WO2005/067817 | 7/2005 |
| WO | WO2006/062725 | 6/2006 |
| WO | WO2007/057739 | 5/2007 |
| WO | WO2007/082115 | 7/2007 |
| WO | WO2008/034077 | 3/2008 |
| WO | WO2008/057720 | 5/2008 |

OTHER PUBLICATIONS

PCT Written Opinion of the International Search Authority for PCT/US2005/000041 Applicant: Ramon Medical Technologies Ltd, Form PCT/ISA/237, dated Apr. 21, 2005 (4 pages).

Holmes et al. "SirolimusEluting Stents vs. Vascular Brachytherapy for InStent Restenosis Within BareMetal Stents" JAMA295 (11): 12641273 Mar. 15, 2006.

Lanning & Shandas, "Development and Validation of Implantable Sensors for Monitoring Function of Prosthetic Heart Valves: in Vitro Studies", Medical & Biological Engineering & Computing, Jul. 2003, vol. 41, issue 4, pp. 416- 424.

Sheth et al. "Subacute Thrombosis and Vascular Injury Resulting From SlottedTube Nitinol and Stainless Steel Stents in a Rabbit Carotid Artery Model" Circulation 94: 17331740.

Stone et al. "PaclitaxelEluting Stents vs.Vascular Brachytherapy for InStent Restenosis Within BareMetal Stents" Jama 295( 11): 12531263.

Wenaweser et al. "Stent thrombosis following baremetal stent implantation: success of emergency percutaneous coronary intervention and predictors of adverse outcome" European Heart Journal 26: 11801187 2005.

* cited by examiner

DEVICES FOR FIXING A SENSOR IN A LUMEN

CROSS-REFERENCE TO RELATED APPLICATIONS

The present application claims priority under 35 U.S.C. §119 to U.S. Provisional Patent Application Ser. No. 60/536,580, entitled "Device for Fixing a Sensor in a Lumen," filed Jan. 13, 2004, the complete contents of which are incorporated herein by reference.

FIELD OF THE DISCLOSURE

The present invention relates to field of medical devices and more specifically to a device for positioning a sensor in a lumen.

BACKGROUND

The use of sensors in body lumens is well known. For example, U.S. Pat. No. 4,485,813 describes a sensor that can be permanently implanted in a specific location within the human body in an implantable medical device such as a pacemaker. In other applications sensors are implanted alone in a body lumen. U.S. Pat. No. 6,645,143, 6,053,873, 6,442,413 and U.S. application 2002/0188207 describe medical monitoring sensors designed to be implanted in the vascular system and is capable of sensing and transmitting via a telemetry link to an external monitor.

The implanted sensors are utilized for monitoring physical, chemical or physiological parameters in the body. The aim of such sensors is to accurately monitor the desired parameter.

The position of the sensor within the lumen can influence the accuracy of the measurement. Positioning of a sensor facing a lumen wall can alter the sensing ability. Furthermore, positioning of a sensor pressing against the lumen wall in blood vessels may encourage responses, such as neo-intimal growth, which can influence and/or impact the long and short terms accuracy of measurements.

U.S. patent application publication No. 2002/0188207 discloses a device and method for anchoring a sensor at the center of the lumen. This concept addresses the issue of tissue growth. However, it is problematic to axially align multiple sensors in the same vicinity of a lumen, since a first sensor would block the further sensor(s) from blood flow through the lumen. Thus, it is desirable, and often functionally necessary, to radially and/or circumferentially off-set the sensors of a multiple sensor arrangement, so that they are not coaxially aligned. On the other hand, it is desirable, and often functionally necessary, to operably connect the individual sensors of a multiple sensor arrangement.

There are several medical procedures that require insertion of catheters or other devices through a body lumen and especially through the vascular system, for example, Swan-Ganz catheter to the pulmonary artery for monitoring hemodynamic parameters. Thus, a sensor implantation device should not prevent accessibility to a desired location within the vascular system.

SUMMARY

One embodiment of the invention is an apparatus for positioning at least one sensor in a body lumen, the body lumen having a wall, the apparatus including a fixation element, a sensor, and a connecting element that connects the sensor to the fixation element. The connecting element extends at least partially into the lumen so that the sensor is located radially inward from the lumen wall. Other and further embodiments and aspects of the invention are disclosed and described herein.

BRIEF DESCRIPTION OF THE DRAWINGS

The present invention will be more fully understood and appreciated from the following detailed description taken in conjunction with the figures, in which.

DETAILED DESCRIPTION

Figure 1A:
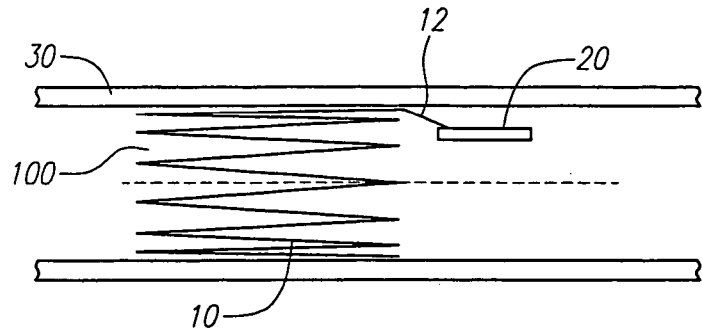
FIGS. 1A-1D are schematic illustrations of a device having a stent-like configured fixation element according to one an embodiment of the invention.

The devices disclosed in the following detailed description enable positioning of an implant such as a sensor, a drug reservoir, or other known and/or convenient device within a lumen at a location which is between the inner lumen wall and the lumen center.

In one embodiment, the device includes a fixation part and an implant that is positioned between the lumen wall and the center of the lumen. The implant can be directly connected to the fixation part. The device can further include a connecting element for connecting between the fixation part and the implant and/or for positioning the implant at the desired location. The implant can be a sensor such as, for example, a pressure sensor that is implanted in blood vessel for monitoring blood pressure or any other known and/or convenient device. However, any known and/or convenient sensor can be used, including, but not limited to, a flow sensor, a radiation sensor, a temperature sensor, an electrical impedance sensor, other physical measurement sensor, an optical sensor for monitoring Hemoglobin concentrations and/or glucose concentrations or any other measurement, or any type of sensor for monitoring chemical species and/or composition, and/or an electrochemical sensor for monitoring various compounds within the bloods, for example, calcium, potassium, sodium and/or any other measurable compound, molecule, atom, and/or ion.

In alternate embodiments, the device can further include a second implant located either in contact with the wall or at the vicinity of the wall or in any other convenient location within a lumen. The second implant can be a second sensor such as, for example, a flow sensor for monitoring flow in the cardiovascular system or an energy source such as a battery or any other known and/or convenient device. The second implant can be connected to the first implant. For example, a first implant which is a sensor can be electrically connected, using an isolated electric wire, to a second implant which is an energy source such as battery for enabling energy transfer from the energy source to the sensor.

In one embodiment, a first implant, which can be a sensor, can be located between the lumen wall and the center of the lumen and a second implant, which can be an energy source, can be located in contact with the lumen wall and electrically connected to the sensor. This configuration enables miniaturizing of the first implant since the energy source is not a part of the sensor.

The insertion of the device into a body lumen can be performed via a catheterization procedure. The device can be mounted on a delivery system, in a compressed configuration so as to enable navigation through the lumen, and delivered through the lumen to the desired deployment site. At the desired deployment site the expandable technique and/or any other known and/or convenient method and/or mechanism.

Other techniques for inserting a device into a lumen, such as making an incision in the lumen and suturing the device at the desired location can be applied. Additionally, the device can be connected to other implants.

Reference is now made to FIGS. 1A-1D illustrating a device that includes a fixation element having a stent-like configuration according to an embodiment of the invention. The devices shown in the embodiments include a fixation element 100, a connecting element 12 and a sensor 20. For convenience and clarity, the lumen 30 is shown in cross-section.

In the embodiment shown in FIG. 1A, fixation element 100 can be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or can be manufactured from any known and/or convenient material using any known and/or convenient method and having any convenient shape. In the embodiment shown in FIG. 1A, the struts 10 cross section can be round, oval, rectangular or any convenient shape. In the embodiment shown in FIG. 1A, the struts are arranged in a zigzag configuration. However in alternate embodiments, the struts can have any convenient configuration. The thickness of struts 10 is in the range of 0.05-0.5 mm. However in alternate embodiments, various other thicknesses can be used. The struts can further includes ridges or hooks for preventing migration within the lumen.

FIG. 1A shows fixation element 100 having a radial zigzag configuration that is in contact with the inner side of the lumen wall. The sensor 20 can be connected to a connecting element 12 for connecting sensor 20 to fixation element 100 and for positioning sensor 20 at a desired location distanced from the lumen wall. The sensor 20 can be located between the lumen wall and the center of the lumen. In some embodiments, the sensor can be distanced from the lumen wall between 0.05 mm and 0.8 r wherein r is the lumen radius. For example, for blood vessel having radius of r=10 mm the sensor can be positioned at a distance of 0.05 to 8 mm from the vessel wall.

In some embodiments, connecting element 12 can be made of metal such as Nickel-Titanium alloy, stainless steel, titanium, cobalt-based alloy, or using tantalum, Gold, Platinum or Platinum-Iridium for enhance radio-opacity, or a polymer including a shape memory polymer with or without the addition of radio-opaque material e.g. barium sulfate, and/or composed of any known and/or convenient material and or made in any know and/or convenient shape using any known and/or convenient method.

Figure 1B:
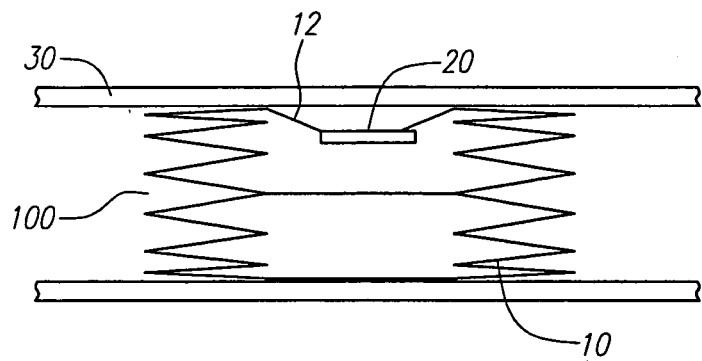
Figure 1C:
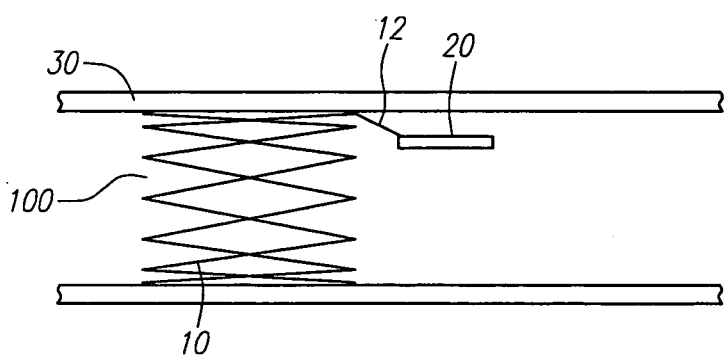
Figure 1D:
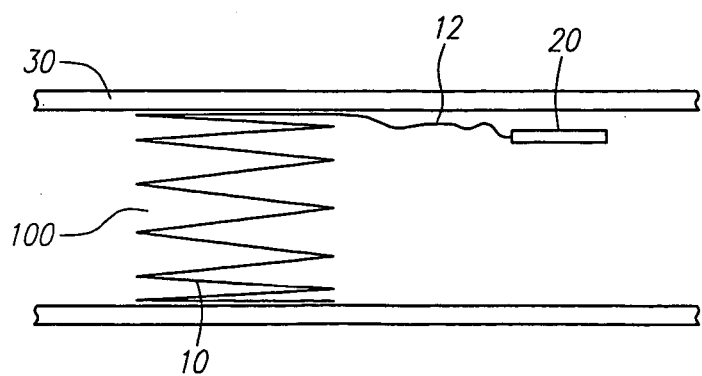

In some embodiments, connecting element 12 can be rigid so as to maintain sensor 20 at constant position or can be flexible as illustrated in FIG. 1D, so as to enable movement of the sensor within the lumen. In alternate embodiments, sensor 20 can be connected directly to strut 10 of fixation element 100. In selected embodiments, the sensor 20, can be located in a position proximal to the fixation element 100 to reduce neo intima and cell proliferation.

In alternate embodiments, sensor 20 can be oriented parallel, perpendicular or at any other angle to the lumen wall. In still further alternate embodiments, the active face of the sensor 20 can be oriented towards the lumen center, the lumen wall or tangential and/or in any other convenient location.

Reference is now made to FIG. 1B, illustrating one configuration of the device having two fixation elements 100 at both sides, proximal and distal to the sensor 20. In the embodiment shown in FIG. 1B, proximal and distal fixation elements 100 can be connected at one or more points and sensor 20 can be connected to fixation element 100 by one connecting element. That is, sensor 20 can be connected to the distal or proximal strut or can be connected to the distal and proximal strut. Sensor 20 can be oriented parallel, perpendicular or at any other angle to the lumen wall. The active face of the sensor 20 can be oriented towards the lumen center, the lumen wall or tangential or in any convenient orientation. In some embodiments, connecting element 12 can be rigid so as to maintain sensor 20 at constant position or can be flexible so as to allow movement of sensor 20.

Reference is now made to FIG. 1C, illustrating an alternate configuration of fixation element 100 in which the struts are configured in a closed cell zigzag arrangement. However in some embodiments, any known and/or convenient strut configuration can be used. Furthermore, it will be appreciated that other configurations can be used.

Figure 2A:
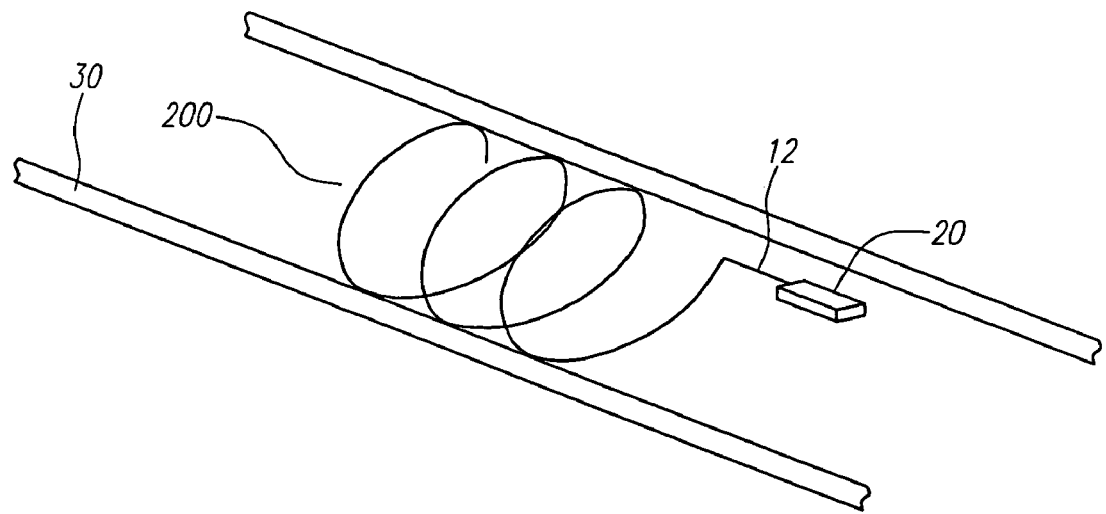
FIGS. 2A-2B are schematic illustrations of a device having a coiled configured fixation element according to another embodiment of the invention.
Figure 2B:
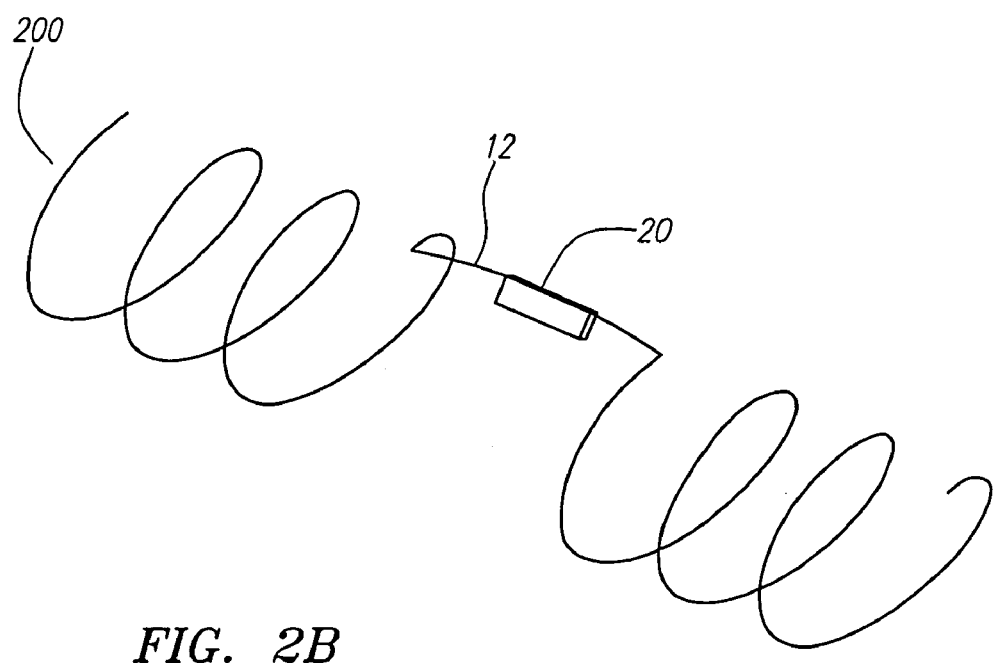

Reference is now made to FIGS. 2A-2B illustrating a device having a coiled fixation element 200 according to an embodiment of the invention. The device can include coiled configured fixation element 200, connecting element 12 and sensor 20. For clarity and convenience the lumen 30 is shown in cross-sectional view.

The coiled fixation element 200 can be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or composed of any known and/or convenient material, in any convenient shape and/or using any known and/or convenient method. The fixation element cross-section may be round, oval, rectangular etc. The thickness of strut 10 of coiled fixation element 200 is in the range of 0.05-0.5 mm. Additionally in selected embodiments, the strut can further includes ridges or hooks for preventing migration within the lumen.

The coiled fixation element 200 configuration can be radial and can be in contact with the lumen wall. The sensor 20 can be connected to a connecting element 12 for connecting sensor 20 to fixation element 200 and/or for positioning sensor 20 at a desired location distanced from the lumen wall. In alternate embodiments, sensor 20 can be connected directly to coil fixation element 200. In various embodiments, the sensor can be located between the lumen wall and the center of the lumen. In alternate embodiments the sensor can be distanced from the lumen wall between 0.05 mm and 0.8 r wherein r is the lumen radius. However in alternate embodiments, the sensor can be located at any convenient distance from the lumen wall. For example, for blood vessel having radius of r=10 mm the sensor can be positioned at a distance of 0.05 to 8 mm of the vessel wall. In selected embodiments, connecting element 12 can be made of metal such as Nickel-Titanium alloy, stainless steel titanium, cobalt-based alloy, or using tantalum, Gold, Platinum or Platinum-Iridium for enhance radio-opacity, or a polymer including a shape memory polymer with or without the addition of radio-opaque material e.g. barium sulfate, or any known and/or convenient material, in any convenient shape and manufactured in any known and/or convenient manner. In selected embodiments, connecting element 12 can be rigid so as to maintain sensor 20 at constant position or can be flexible so as to allow movement of sensor 20.

The sensor 20 may be oriented parallel, perpendicular or at any other angle to the lumen wall. The active face of the sensor 20 can be oriented towards the lumen center, the lumen wall, tangential to the lumen wall or at any other convenient angle within the lumen. In selected embodiments, sensor 20 can be oriented parallel, perpendicular or at any other angle to the lumen wall.

Reference is now made to FIG. 2B, illustrating a device having coiled fixation element 200 at both sides, of sensor 20. In the embodiment shown in FIG. 2B, proximal and distal coiled fixation element 200 can be connected at one or more points. Connecting element 12 can be rigid so as to maintain sensor 20 at constant position or can be flexible so as to allow movement of sensor 20. Additionally, sensor 20 can be oriented parallel, perpendicular or at any other angle to the lumen wall. The active face of the sensor 20 can be oriented towards the lumen center, the lumen wall or tangential. Furthermore, sensor 20 can be oriented parallel, perpendicular or at any other angle to the lumen wall. As will be apparent to those skilled in the art, other configurations can be used.

Reference is now made to FIGS. 3A-3D, illustrating a device having a wing-configured fixation element. In the embodiments shown in FIGS. 3A-3D, the device includes wing-configured fixation element 300, connecting element 12 and a sensor 20. For convenience and clarity, the lumen 30 is shown in cross-sectional view.

The wing-configured fixation element 300 may be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material, e.g. barium sulfate, or can be comprised of any known and/or convenient material, can be manufactured using any known and/or convenient shape and can be made using any known and/or convenient method.

The struts 10 of wing configured fixation element 300 may have a round, oval, rectangular etc. cross section. The thickness of struts 10 is in the range of 0.05-0.5 mm. The thickness of the struts may be any convenient thickness. Additionally, the struts can further include ridges or hooks for preventing migration within the lumen.

Figure 3A:
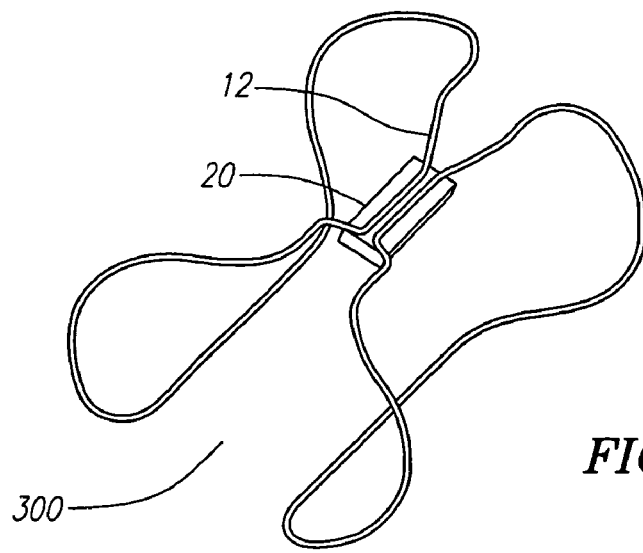
FIGS. 3A-3D are schematic illustrations of a device having a wing configured fixation element according to yet another embodiment of the invention.
Figure 3B:
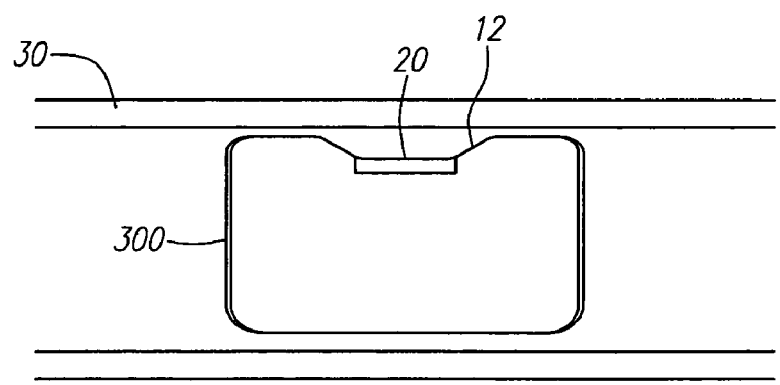
Figure 3C:
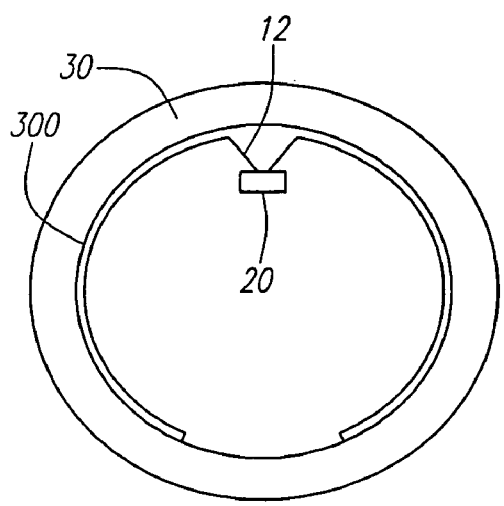

FIG. 3A is a three dimensional view of the device having wing configured fixation element 300 and FIGS. 3B and 3C illustrate longitudinal and lateral cross sections, respectively.

The sensor 20 may be connected to a connecting element 12 for connect sensor 20 to fixation element 300 and for position sensor 20 at a desired location distanced from the lumen wall. In other embodiment sensor 20 can be connected directly to fixation element 300. The sensor can be located between the lumen wall and the center of the lumen. In one embodiment the sensor can be distanced from the lumen wall between 0.05 mm and 0.6 r wherein r is the lumen radius. For example, for blood vessel having radius of r=10 mm the sensor can be positioned at a distance of 0.05 to 8 mm of the vessel wall. However in alternate embodiments, the sensor can be located at any convenient location within the lumen. Additionally, connecting wire 12 can be made of metal such as Nickel-Titanium alloy, stainless steel titanium, cobalt-based alloy, or using tantalum, Gold, Platinum or Platinum-Iridium for enhance radio-opacity, or a polymer including a shape memory polymer with or without the addition of radio-opaque material e.g. barium sulfate, or any known and/or convenient material, made in any convenient shape using any known and/or convenient manufacturing process.

In alternate embodiments, connecting element 12 can be made of metal such as Nickel-Titanium alloy, stainless steel titanium, a polymer or any known and/or convenient material. The connecting element 12 can be rigid so as to maintain sensor 20 at constant position or can be flexible so as to enable movement of the sensor within the lumen. In alternate embodiments, sensor 20 can be connected directly to fixation element 300.

In the embodiments shown in FIGS. 3A-3C, sensor 20 can be oriented parallel, perpendicular or at any other angle to the lumen wall. The active face of the sensor 20 can be oriented towards the lumen center, the lumen wall, tangential to the lumen wall or at any other convenient angle.

Figure 3D:
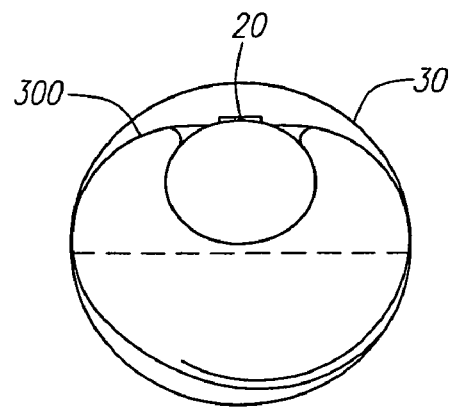

FIG. 3D illustrates a lateral cross section of another configuration of the wing fixation element 300. In the configuration shown in FIG. 3D, the sensor is at the same level as the strut. In those embodiments in which the struts 10 are made of superelastic Nickel-Titanium alloy, intermediate levels of expansion can be implemented such that the predetermined distances of the sensor from the vessel wall can be achieved.

Figure 4A:
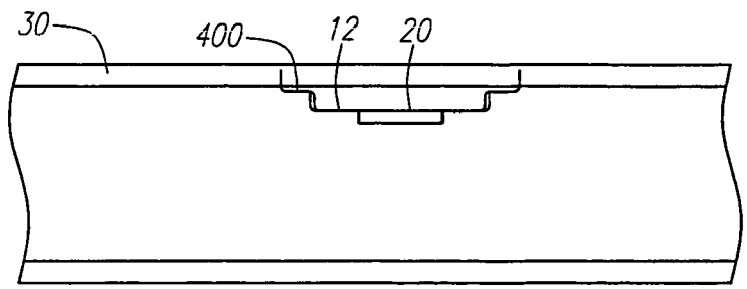
FIGS. 4A-4C are schematic illustrations of a device having a hook configured fixation element according to still another embodiment of the invention FIG. 5 are schematic illustrations of a device having two implants according to a still further embodiment of the invention
Figure 4B:
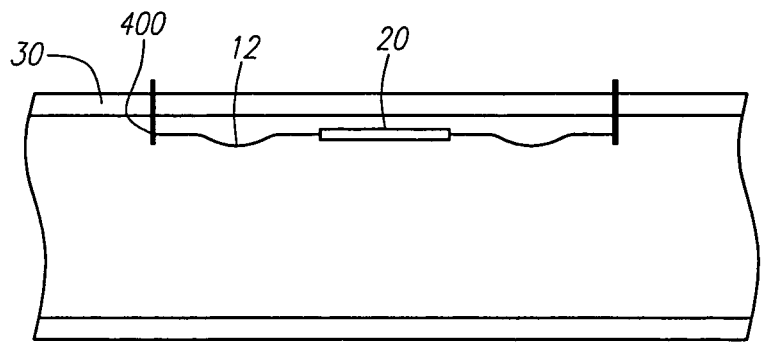
Figure 4C:
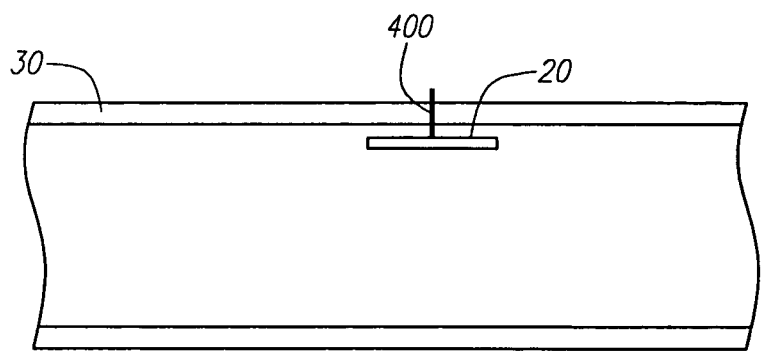

Reference is now made to FIGS. 4A-4C, illustrating a device having a hook configured fixation element according to an embodiment of the invention. The device includes hook configured fixation element 400, connecting element 12 and a sensor 20. Cross section of lumen 30, for example a blood vessel, is shown.

Fixation element 400 can be manufactured from a wire, a laser cut or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or of any known and/or convenient material, can be manufactured in any convenient shape using any known and/or convenient method of manufacture. The strut of fixation element 400 cross section can be round, oval, rectangular or have any convenient shape The thickness of struts is in the range of 0.05-1 mm. The struts can have any convenient thickness and/or dimensions. Additionally, the struts can further includes ridges or hooks for anchoring fixation element 400 within the lumen and preventing migration within the lumen.

FIG. 4A shows a device having a hook configured fixation element 400 that is hooked into the lumen wall at least at two points. Hooking can be at the longitudinal axis of the lumen as shown in FIG. 4A or at the transverse axis (not shown).

The sensor 20 can be connected to a connecting wire 12, which is configured so as to distances the sensor from the lumen wall. The connecting wire 12 is connected to the fixation element 400. The sensor can be located between the lumen wall and the center of the lumen. In one embodiment the sensor can be distanced from the lumen wall between 0.05 mm and 0.8 r wherein r is the lumen radius. For example, for blood vessel having radius of r=10 mm the sensor can be positioned at a distance of 0.05 to 8 mm of the vessel wall. However in alternate embodiments, the sensor can be located at any convenient location within the lumen.

Connecting element 12 can be made of metal such as Nickel-Titanium alloy, stainless steel titanium, cobalt-based alloy, or using tantalum, Gold, Platinum or Platinum-Iridium for enhance radio-opacity, or a polymer including a shape memory polymer with or without the addition of radio-opaque material e.g. barium sulfate or any known and/or convenient material, can have any convenient shape and can be manufactured using any convenient manufacturing process. Connecting element 12 can be rigid so as to maintain sensor 20 at constant position or can be flexible as illustrated in FIG. 4B, so as to enable movement of the sensor within the lumen. In other embodiment sensor 20 can be connected directly to fixation element 400.

The sensor 20 can be oriented parallel, perpendicular or at any other angle to the lumen wall. The active face of the sensor 20 can be oriented towards the lumen center, the lumen wall, tangential to the lumen wall or at any other convenient angle.

Reference is now made to FIG. 4C, illustrating another configuration of fixation element 400 in which the fixation element 400 is inserted in the lumen similarly to the insertion of a drawing pin. The sensor 20 can be directly connected to fixation element 400 or connected via a connecting wire.

The sensor 20 can be oriented parallel, perpendicular or at any other angle to the lumen wall. The active face of the sensor 20 can be oriented towards the lumen center, the lumen wall, tangential to the lumen wall or any other convenient angle. Additionally, it will be appreciated that other configurations can be used.

Figure 5:
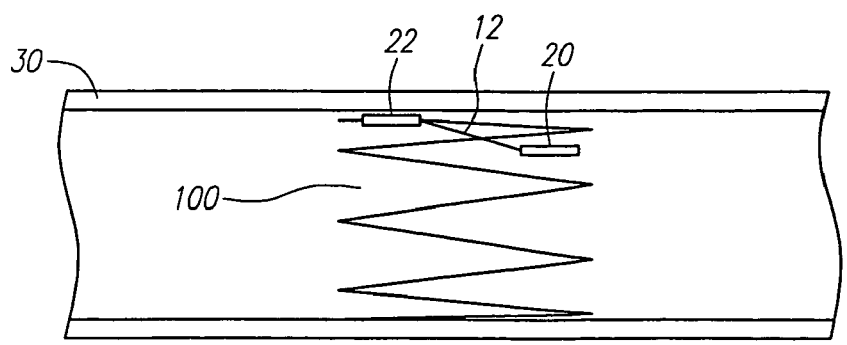

Reference is now made to FIG. 5 which is a schematic illustration of a device having two implants according to an embodiment of the invention. The device includes a fixation element 100, a first implant 20, a second implant 22, and a connecting element 12. For convenient and clarity, the lumen, which can be a blood vessel, is shown in cross-section.

It will be appreciated that fixation element 100 can have any other configuration such as, for example, coil, wing, hook and/or any other known and or convenient configuration.

A first implant 20 may be located between the lumen wall and the center of the lumen. First implant 20 can be distanced from the lumen wall between 0.05 mm and 0.8 r wherein r is the lumen radius. For example, for blood vessel having radius of r=10 mm the first implant can be positioned at a distance of 0.05 to 8 mm of the vessel wall. Second implant 22 can be in contact with the lumen wall or distances from the lumen wall. However in alternate embodiments, the first and second implants can be located at any convenient locations within the lumen and relative to each other.

The first implant 20 and second implant 22 may be connected by connecting element 12. Second implant 22 can be directly connected to fixation element 100 or connected through an additional connecting element.

The connecting element 12 may be made of metal such as Nickel-Titanium alloy, stainless steel titanium, cobalt-based alloy, or using tantalum, Gold, Platinum or Platinum-Iridium for enhance radio-opacity, or a polymer including a shape memory polymer with or without the addition of radio-opaque material e.g. barium sulfate, or of any other know and/or convenient material.

The connecting element 12 may be rigid so as to maintain first implant 20 at constant position or can be flexible so as to enable movement of first implant 20 within the lumen. Connecting element 12 that connects first implant 20 to second implant 22 can be a metallic or a plastic tube that includes an electric wire for enabling electric communication between first and second implants. The connection between first implant 20 and second implant 22 can be achieved using mechanical means, crimp, adhesives, welding or any other convenient mechanism and/or material. In alternate embodiments, the connection between the first implant 20 and second implant 22 can be wireless, wired or made in any other known and/or convenient manner. Furthermore, in embodiments in which the second implant 22 is physically connected with the first implant and/or the fixation element 100, the connection element can support both the first implant and the second implant. Alternately, each implant can have an separate connection element 12 to connect the implant with the fixation element.

In one embodiment first implant 20 can be a sensor such as pressure sensor and second implant 22 can be an energy source such as a battery. The sensor and the battery can be connected by electric wire for enabling energy transfer from the battery to the sensor.

While the invention is susceptible to various modifications, and alternative forms, specific examples thereof have been shown in the drawings and are herein described in detail. It should be understood, however, that the invention is not to be limited to the particular embodiments or methods disclosed, but to the contrary, the invention is to cover all modifications, equivalents and alternatives falling within the scope of the appended claims.

The invention claimed is:

1. An apparatus for positioning within a body lumen having a wall, the apparatus comprising:
   a fixation element configured to attach to the lumen wall;
   a first sensor adapted to measure blood pressure within the body lumen;
   a first elongated connecting element connecting the first sensor to the fixation element, such that, when the fixation element is attached to the lumen wall, the first connecting elements extends from the fixation element at least partially into the lumen so that at least a portion of the first sensor is suspended inwadly away from and located radially inward from the lumen wall such that blood within the body lumen flows between the lumen wall and the first sensor;
   a second sensor; and
   a second elongated connecting element connecting the second sensor to the fixation element, such that, when the fixation element is disposed within the lumen, the second connecting element extends from the fixation element along a longitudinal axis of the second connecting element at least partially into the lumen so that the second sensor is located radially inward from the lumen wall.

2. The apparatus of claim 1, wherein, when the fixation element is disposed within the lumen, the first sensor is located at least approximately 0.05 mm away from the lumen wall.

3. The apparatus of claim 2, wherein, when the fixation element is disposed within the lumen, the first sensor is located less than approximately 0.8 r away from the lumen wall, wherein r represents the lumen radius.

4. The apparatus of claim 1, wherein the first connecting element is connected to the fixation element.

5. The apparatus of claim 1, further comprising a second elongated connecting element connecting the first sensor to the fixation element.

6. The apparatus of claim 5, wherein, when the fixation element is disposed within a lumen, the first connecting element at least partially extends in a first direction along a longitudinal axis of the lumen, and the second connecting element extends at least partially in a second direction along the longitudinal lumen axis that is substantially opposite the first direction.

7. The apparatus of claim 1, wherein the first and second sensors each measure at least one of blood pressure, blood temperature and blood composition.

8. The apparatus of claim 1, wherein the first connecting element is a wire.

9. The apparatus of claim 1, wherein, when the fixation element is disposed within the lumen, the first connecting element includes one or more bends that extend from the fixation element inwardly from the lumen wall.

10. The apparatus of claim 1, wherein, when the fixation element is disposed within the lumen, a longitudinal axis of the first connecting element is angled relative to a longitudinal axis of the lumen.

11. The apparatus of claim 1, wherein the first sensor is disposed on a distal end of the first connecting element.

12. The appartus of claim 1, wherein the first connecting element is resilient.

13. The apparatus of claim 1, further comprising another fixation element, wherein the first connecting element connects the first sensor between the fixation element and the other fixation element.

14. The apparatus of claim 1, wherein the fixation element is configured as a stent.

15. The apparatus of claim 1, wherein the fixation element is configured as a coil.

16. The apparatus of claim 1, wherein the fixation element is configured as one of a wing and a hook.

17. The apparatus of claim 1, wherein, when the fixation element is disposed within a lumen, the first sensor and the second sensor are positioned such that they are other than co-axially aligned with a longitudinal axis of the lumen.

18. A method of using the apparatus of claim 1, comprising:
  anchoring the fixation element to the lumen wall; and
  locating the first sensor radially inward from the lumen wall.

19. An apparatus for positioning within a blood vessel having a vessel wall, comprising:
  an expandable, stent-like fixation element configured to radially expand from a collapsed position to an expanded position within the blood vessel, the fixation element adapted to assert a radial force against and contact the vessel wall in the expanded position;
  a sensor; and
  a plurality of elongated connecting elements connecting the sensor to the fixation element so that the sensor is suspended inwardly away from the vessel wall and positioned at a location between the vessel wall and a center of the blood vessel when the fixation element contacts the vessel wall to allow blood within the blood vessel to flow between the vessel wall and the sensor.

20. The apparatus of claim 19, wherein, when the fixation element is disposed within the blood vessel, the sensor is positioned at least 0.05 mm away from the vessel wall and less than 0.8 r away from the vessel wall, wherein r is the radius of the blood vessel.

21. The apparatus of claim 19, wherein the sensor is a pressure sensor capable of measuring a pressure of blood within the vessel.

22. The apparatus of claim 19, wherein the fixation element is made from at least one of a wire, a laser-cut tube, and a sheet of metal.

23. The apparatus of claim 19, wherein the fixation element has a coiled configuration or a wing configuration.

24. An apparatus for measuring blood pressure within a blood vessel having a vessel wall, the apparatus comprising:
  an expandable, generally cylindrical fixation element configured to radially expand from a collapsed position, capable of delivery and navigation through the blood vessel, to an expanded position within the blood vessel, the fixation element adapted to contact the vessel wall in the expanded position;
  a pressure sensor adapted to measure blood pressure within the blood vessel; and
  a first connecting element coupling the sensor to the fixation element, such that, when the fixation element contacts the vessel wall in the expanded position, the first contacting element extends from the fixation element at least partially into the blood vessel so that the sensor is suspended inwardly away from the vessel wall and is located between the vessel wall and a center of the blood vessel to allow blood within the blood vessel to flow between the vessel wall and the sensor.

25. The apparatus of claim 24, further comprising an energy source coupled to the fixation element and to the pressure sensor.

26. The apparatus of claim 24, wherein the fixation element has a stent-like configuration.

27. The apparatus of claim 24, wherein the fixation element has a coiled configuration or a wing configuration.

28. The apparatus of claim 24, wherein substantially all of the fixation element is adapted to contact the vessel wall.

29. The apparatus of claim 24, wherein the fixation element is made from at least one of a wire, a laser-cut tube, and a sheet of metal.

* * * * *

UNITED STATES PATENT AND TRADEMARK OFFICE
CERTIFICATE OF CORRECTION

PATENT NO. : 7,572,228 B2
APPLICATION NO. : 11/034502
DATED : August 11, 2009
INVENTOR(S) : Lone Wolinsky et al.

It is certified that error appears in the above-identified patent and that said Letters Patent is hereby corrected as shown below:

Column 1
Line 26, delete "No." and insert therefor --Nos.--
Line 29, delete "is" and insert therefor --are--
Line 40, delete "terms" and insert therefor --term--
Line 41, delete "U.S." and insert therefor --United States--
Line 41, delete "patent" and insert therefor --Patent--
Line 41, delete "application" and insert therefor --Patent Publication--
Line 41, delete "publication" and insert therefor --Publication--
Line 41, insert --Serial-- between Publication and No. --Publication Serial No.--

Column 2
Line 22, insert a --.-- after invention --invention.--
Line 23, delete "are" and insert therefor --is--
Line 25, insert a --.-- after invention --invention.--
Line 41, delete "vessel" and insert therefor --vessels--

Column 3
Line 40, delete "includes" and insert therefor --include--
Line 51, insert --a-- between for and blood vessel --for a blood vessel--
Line 56, delete "Gold" and insert therefor --gold--
Line 56, delete "Platinum" and insert therefor --platinum--
Line 57, delete "Platinum-Iridium" and insert therefor --platinum-iridium--
Line 57, delete "enhance" and insert therefor --enhanced--

Column 4
Line 47, delete "includes" and insert therefor --include--
Line 63, delete "of" and insert therefor --off--
Line 66, delete "Gold" and insert therefor --gold--
Line 66, delete "Platinum" and insert therefor --platinum--
Line 66, delete "Platinum-Iridium" and insert therefor --platinum-iridium--
Line 66, delete "enhance" and insert therefor --enhanced--

Column 5
Line 53, delete "connect" and insert therefor --connecting--
Line 54, delete "position" and insert therefor --positioning--
Line 60, insert --a-- between for and blood vessel --for a blood vessel--
Line 61, delete the second "of" and insert therefor --off--
Line 66, delete "Gold" and insert therefor --gold--
Line 66, delete "Platinum" and insert therefor --platinum--
Line 66, delete "Platinum-" and insert therefor --platinum- --
Line 67, delete "Iridium" and insert therefor --iridium--
Line 67, delete "enhance" and insert therefor --enhanced--

Column 6
Line 40, insert a --.-- after shape --shape.--
Line 43, delete "includes" and insert therefor --include--
Line 51, delete "distances" and insert therefor --distance--
Lines 56-57, insert --a-- between for and blood vessel --for a blood vessel--
Line 58, delete the second "of" and insert therefor --off--
Line 63, delete "Gold" and insert therefor --gold--
Line 63, delete "Platinum" and insert therefor --platinum--
Line 63, delete "Platinum-Iridium" and insert therefor --platinum-iridium--
Line 64, delete "enhance" and insert therefor --enhanced--

Column 7
Line 27, delete "convenient" and insert therefor --convenience--
Line 35, insert --a-- between for and blood vessel --for a blood vessel--
Line 37, delete "of" and insert therefor --off--
Line 38, delete "distances" and insert therefor --distanced--
Line 48, delete "Gold" and insert therefor --gold--
Line 48, delete "Platinum" and insert therefor --platinum--
Line 48, delete "Platinum-Iridium" and insert therefor --platinum-iridium--
Line 49, delete "enhance" and insert therefor --enhanced--
Line 51, delete "know" and insert therefor --known--

Column 8
Line 2, delete "an" and insert therefor --a--
Line 28, Claim 1: Replace "elements" with --element--
Line 30, Claim 1: Replace "inwadly" with --inwardly--

Signed and Sealed this

Sixteenth Day of March, 2010

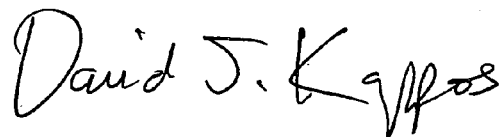

David J. Kappos
*Director of the United States Patent and Trademark Office*